(12) United States Patent
Plaia et al.

(10) Patent No.: US 6,497,711 B1
(45) Date of Patent: Dec. 24, 2002

(54) THERECTOMY DEVICE HAVING A LIGHT WEIGHT DRIVE SHAFT AND AN IMAGING DEVICE

(75) Inventors: Mark Plaia, Santa Cruz, CA (US); Robert L. Barry, Kirkland, WA (US); Daniel M. Lafontaine, Plymouth, MN (US)

(73) Assignee: Scimed Life Systems, Inc., Maple Grove, MN (US)

( * ) Notice: Subject to any disclaimer, the term of this patent is extended or adjusted under 35 U.S.C. 154(b) by 57 days.

(21) Appl. No.: 09/639,873

(22) Filed: Aug. 16, 2000

(51) Int. Cl.$^7$ .............................................. A61B 17/22
(52) U.S. Cl. ........................ 606/159; 606/167; 606/170
(58) Field of Search ........................... 623/1.11; 606/99, 606/108, 159, 167, 170, 171, 194, 15, 37, 39, 45, 46; 604/27, 28, 36, 507, 508, 510, 93.01, 95.01, 164.13, 264

(56) References Cited

U.S. PATENT DOCUMENTS

| | | | |
|---|---|---|---|
| 5,360,432 A | * 11/1994 | Shturman | 606/159 |
| 5,766,192 A | * 6/1998 | Zacca | 606/159 |
| 5,941,869 A | * 8/1999 | Patterson et al. | 604/22 |
| 5,976,107 A | * 11/1999 | Mertens et al. | 604/164.13 |
| 6,001,112 A | * 12/1999 | Taylor | 606/159 |
| 6,156,046 A | * 12/2000 | Passafaro et al. | 128/898 |
| 6,183,487 B1 | * 2/2001 | Barry et al. | 606/159 |

\* cited by examiner

Primary Examiner—David J. Isabella
Assistant Examiner—Urmi Chattopadhyay
(74) Attorney, Agent, or Firm—Christensen, O'Connor, Johnson, Kindness, PLLC

(57) ABSTRACT

An atherectomy device having the ability to create variably sized lumens in a vessel. An ablation burr rotated by a drive shaft is routed through a control shaft having a bend in its distal end. The control shaft is in turn routed through a surrounding guide catheter. By extending or retracting the bend of the control shaft into the distal end of the guide catheter, the lateral displacement of the ablation burr is varied. A lumen in a vessel is created by rotating the control shaft within the surrounding guide catheter. In addition, the atherectomy device may include an integrated imaging sensor contained within a separate lumen of the catheter surrounding the drive shaft. The imaging sensor provides images of the interior of the vessel wall to determine if an occlusion has been removed by operation of the ablation burr. The catheter may include a self-expanding stent at its distal end to force the ablation burr against a vessel wall in order to create various sized lumens in a patient's vasculature. Finally, the drive shaft that rotates the ablation burr is made of a lightweight polymeric material such as a liquid crystal polymer having fibers that are braided to provide desired torque and flexibility characteristics of the drive shaft.

7 Claims, 5 Drawing Sheets

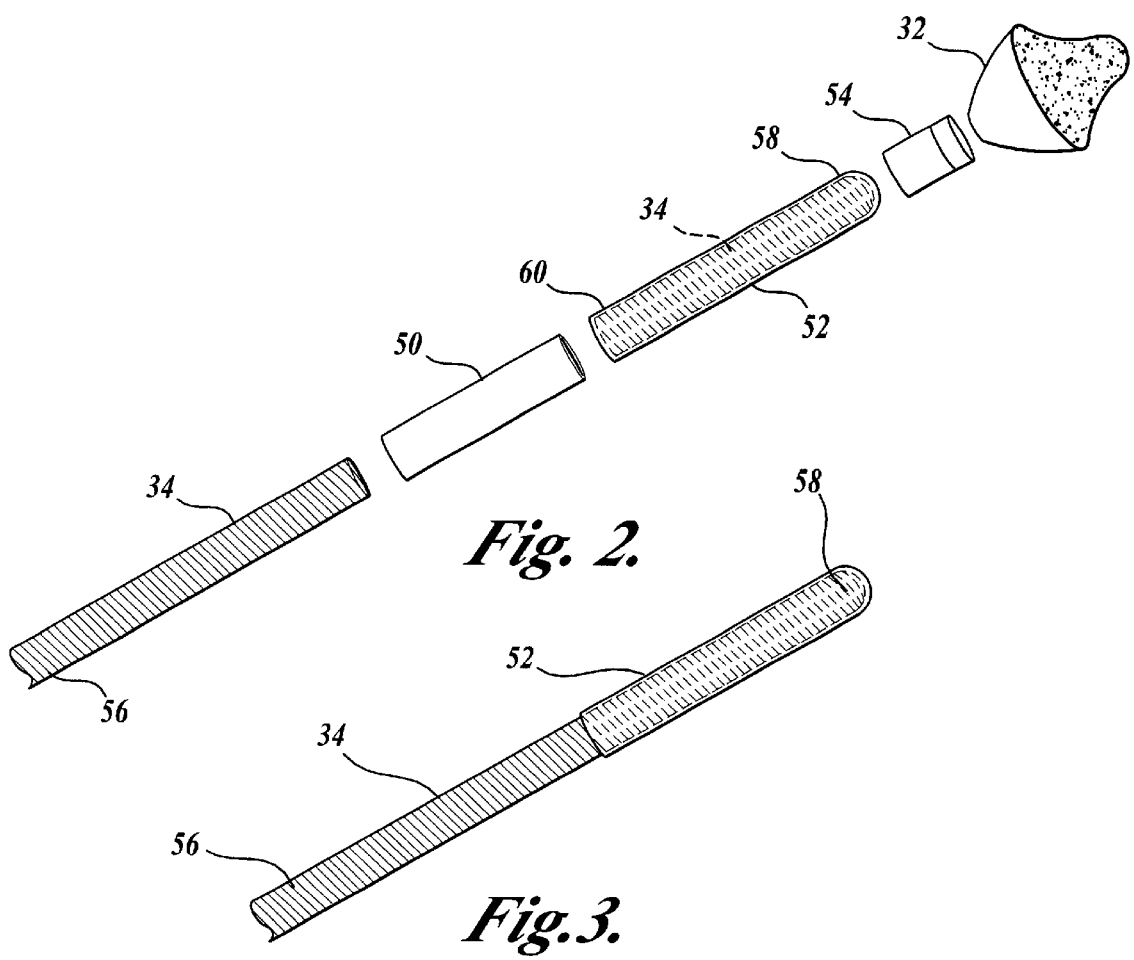
Fig. 2.
Fig. 3.
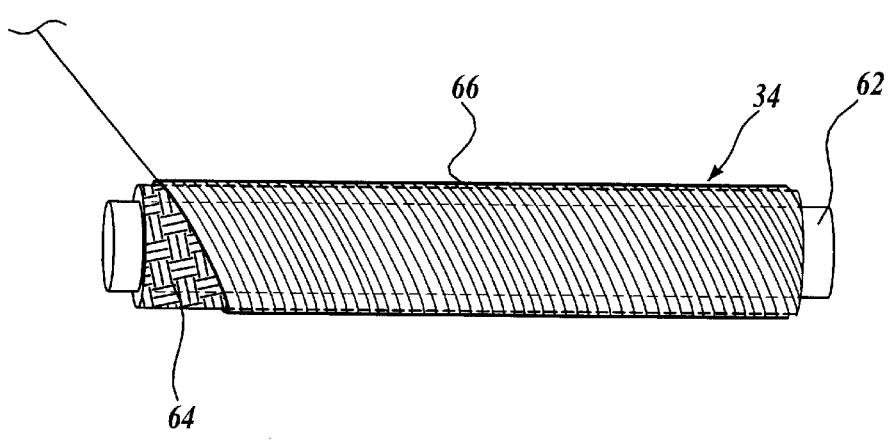
Fig. 4.

THERECTOMY DEVICE HAVING A LIGHT WEIGHT DRIVE SHAFT AND AN IMAGING DEVICE

FIELD OF THE INVENTION

The present invention relates to medical devices in general, and in particular to atherectomy devices for removing occluding material from a patient's blood vessels.

BACKGROUND OF THE INVENTION

Vascular diseases, such as arteriosclerosis and the like, have become quite prevalent in modern day. These diseases may manifest themselves in a number of ways, often requiring different forms or methods of treatment for curing the adverse effects of the diseases. For example, vascular diseases may take the form of deposits or growths in a patient's vasculature which may restrict, in the case of a partial occlusion, or, stop, in the case of a total occlusion, blood flow to a certain portion of the patient's body. This can be particularly serious if, for example, such an occlusion occurs in a portion of the vasculature that supplies vital organs with blood or other necessary fluids.

To treat these diseases, a number of different invasive and minimally invasive therapies have been developed. For example, cardiac bypass surgery is now a commonly performed procedure whereby an occluded cardiac artery is bypassed with a segment of a healthy blood vessel that is obtained from elsewhere in the body. While this procedure is generally successful, it is fairly traumatic because the entire chest cavity of the patient must be opened to access the occluded vessel. Therefore, the procedure is generally not performed on frail or elderly patients.

As an alternative to bypass surgery, it is also fairly common to treat occluded vessels using an intravascular device. Such treatment devices, sometimes referred to as atherectomy or ablation devices, use a variety of material removal means, such as rotating cutters or ablaters, to remove the occluding material. The material removal means, such as a rotatable burr, is typically coupled to an electric motor or air turbine via a drive shaft that extends out of the patient's body. The drive shaft is rotated and the burr is advanced through the occluding vessel. The rotating burr grinds the occluding material into sufficiently small fragments that are removed by the body, rather than merely displacing or reforming the material in the vessel as in a balloon angioplasty procedure.

One problem faced by physicians when performing an atherectomy procedure is determining if all of the stenosis has been ablated by the ablation burr while the ablation burr is within the occluded area. While imaging techniques such as fluoroscopy or external ultrasound have been developed to image a person's vasculature, these techniques generally cannot resolve a thin layer of occluding material that remains on a vessel wall. Therefore, there is a need for an atherectomy device that can image the interior of a patient's vasculature without removing the ablation burr from the occluded site.

Yet another problem that occurs with conventional atherectomy devices is the fact that they can only create lumens of a fixed size. Therefore, if a physician wants to increase the size of a lumen, the driveshaft and burr have to be removed from the patient and replaced with a larger diameter burr. Therefore, there is a need for an atherectomy device that can create various sized lumens with a single burr.

Another area for improvement of conventional atherectomy devices is with the driveshaft. As indicated above, rotational energy is transferred from the motor or turbine to the ablation burr with a drive shaft. Most drive shafts are constructed of wound steel. For example, a Rotoblator® atherectomy device as developed by Boston Scientific uses a wound steel coil to transmit the rotational energy created outside of the patient's body to the burr located within a blood vessel lumen or other body channel. Currently, in order to provide sufficient torque carrying capacity, flexibility, and strength the drive shaft is constructed of three steel wires, each of which is 0.006 inches in diameter, that are wound into a coil configuration.

Drive shaft flexibility affects how the drive shaft is controlled and performs in the patient. While a stiff drive shaft is easily advanced through vasculature, it may not easily conform to the vasculature. A drive shaft that is too flexible, however, may stall as it is being advanced. Additionally, a drive shaft having rough edges may not advance smoothly through the stenosis being ablated. For example, tissue could possibly become trapped within the coils of the drive shaft thereby restricting movement of the drive shaft and adversely affecting control. Therefore, it is desirable to improve the drive shaft to be smaller, more flexible and smoother than currently available drive shafts.

SUMMARY OF THE INVENTION

An atherectomy device according to the present invention allows images of an interior vessel wall to be obtained as ablation is occurring in order to ensure that substantially all occluding material is removed from a vessel during an ablation procedure. In one embodiment of the invention, an atherectomy device includes an integrated imaging sensor such as an intravascular ultrasonic transducer. The transducer is preferably disposed on the distal end of a guide wire. The guide wire is routed through a separate lumen of a guide catheter in which an ablation device is routed.

In accordance with another aspect of the present invention, the atherectomy device includes an expandable distal end that forces an ablation burr against a vessel wall such that a single device can be used to create various sized lumens in a patient's vasculature.

In accordance with another aspect of the present invention, the diameter of a lumen that can be created in the vessel is continuously variable by routing the ablation device through a control shaft having a predefined bend at its distal end. The bend in the control shaft is extended from or drawn into a lumen of a surrounding guide catheter. The bend in the control shaft displaces an ablation burr laterally in a vessel depending upon the amount of the bend that extends distally from the end of the surrounding guide catheter. To create a lumen in a vessel, the control shaft is rotated within the surrounding guide catheter.

In accordance with another aspect of the invention, a drive shaft that rotates an ablation burr is made of a lightweight polymeric material such as a liquid crystal polymer. Fibers of the liquid crystal polymer are braided or wound to optimize the torque or flexibility aspects of the drive shaft as needed.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein:

FIG. 2 illustrates a partially elastomer covered drive shaft in accordance with another embodiment of the invention;

FIG. 3 is a view of a drive shaft partially covered by an elastomeric material in accordance with another aspect of the present invention;

FIG. 4 is a more detailed view of an ablation burr and imaging transducer combined in one atherectomy device;

DETAILED DESCRIPTION OF THE PREFERRED EMBODIMENT

Figure 1:
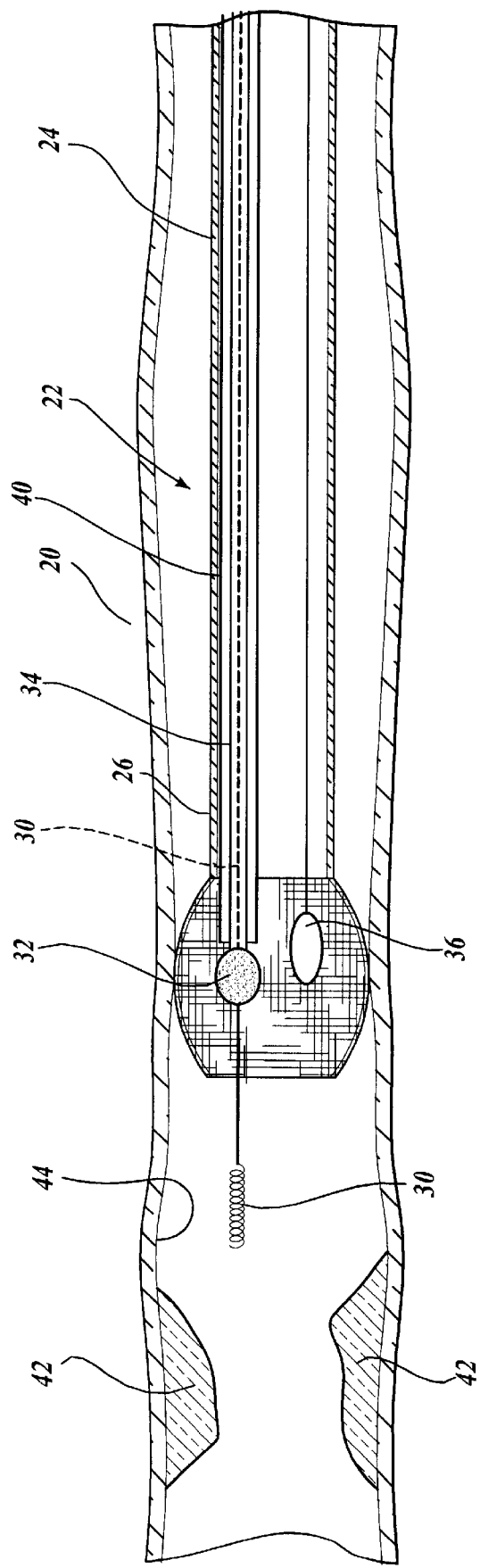
FIG. 1 illustrates a multi-function atherectomy device in accordance with one embodiment of the invention.

FIG. 1 illustrates an atherectomy device 20 in accordance with one embodiment of the present invention. The atherectomy device 20 is routed through a catheter 22 from a position outside of the patient's body to a point near the site of a stenosis 42 in a patient's vessel 44. The catheter 22 has a proximal end 24 that remains outside of the patient's body and a distal end 26 that is located near the stenosis. Extending through the catheter 22 is a guide lumen 40 containing a drive shaft 34. Disposed at a distal end of the drive shaft 34 is an ablation burr 32 that, when rotated by the drive shaft 34, ablates the stenosis 42. The drive shaft 34 is coupled at its proximal end to a source of rotational motion such as an electrical motor or gas turbine (not shown) that rotates the drive shaft 34 at high speed, e.g., between 20,000 and 250,000 rpm. In one embodiment of the invention, the drive shaft is routed over a guide wire 30 having a proximal end and a distal end. The guide wire 30 can be steered by a physician in order to guide the ablation burr 32 through the stenosis 42.

FIG. 2 illustrates a more detailed view of the drive shaft 34 of the present invention. As indicated above, one potential problem with conventional coiled drive shafts is that tissue or plaque may become trapped in the spaces between the coil windings. To reduce the likelihood of that condition occurring, the drive shaft 34 is divided into a proximal end 56 and a distal end 58. The proximal end 56 of the drive shaft 34 is coupled to the distal end 58 of a drive shaft 34 by a coupler 50. In one embodiment of the invention, the proximal end 56 and distal end 58 of the drive shaft 34 are laser welded to the coupler 50. However, it will be appreciated that the drive shaft may be connected to the coupler in many different ways. For example, the drive shaft could be threaded onto the coupler or adhesively bonded to the coupler. The distal end 58 of the drive shaft 34 is covered by an elastomeric material 52 in order to cover the coils 60 of the drive shaft 34. In one embodiment of the invention the elastomer is silicone and is molded over the coils 60 of the steel drive shaft, although other elastomers such as urethane could be used.

The elastomeric material 52 may be placed on the drive shaft 34 using any method that will adhere the elastomeric material 52 to the drive shaft 34. For example, the elastomeric material 52 may be molded onto the distal end of the drive shaft 34 or heat shrunk onto the distal end drive shaft 34. To reduce the likelihood that the elastomeric material will peel back as the drive shaft is rotated, the distal end 58 of the drive shaft 34 may include a burr coupler 54. The burr coupler preferably includes a shoulder region that overlays the end of elastomeric material to prevent its peeling back as the drive shaft is rotated and advanced into the patient's vessel. The burr coupler 54 also includes a distal post to which the ablation burr is secured either by an adhesive, by welding or by other mechanical means. The advantage of the two part drive shaft 34 is that the distal end 58 may be made more flexible than the proximal end 56. Therefore, the drive shaft can have the required stiffness to be routed through the vasculature, while being flexible enough to be routed in the vessels at the site of an occlusion. If the distal end is to be coated with an elastomeric coating, the stiffness of the distal end 58 should take into account the additional stiffness imparted by the coating.

FIG. 3 illustrates an alternative embodiment of a drive shaft according to the present invention. In this embodiment, an elastomeric material is coated directly on the distal end 58 of a unitary drive shaft 34. As discussed above, the elastomeric material may be a variety of different materials including silicone and urethane. When coating a single drive shaft, a portion of the distal end is preferably kept free of the elastomeric coating in order to provide a clean surface to which the ablation burr 32 can be attached.

Another embodiment of the present invention is shown in FIG. 4. Here, the drive shaft 34 is constructed using an advanced polymeric material. For example, a liquid crystal polymer (LCP) material may be used to construct a drive shaft 34 that has good torque carrying capacity and is lightweight. A suitable LCP material is Vectran®, made by Celanese, a division of Hoechst Group. Vectran® has a tensile strength similar to that of steel used in atherectomy drive shafts but only weighs approximately 18% as much as steel. Vectran® fibers also allow a plurality of configurations of drive shaft construction due to the fibrous nature of the material. For example, in one embodiment of the invention, the Vectran® fibers are braided or wound over a mandrel 62 to create a drive shaft having approximately the same diameter size as drive shafts currently used in atherectomy devices but having a lighter weight and greater strength allowing the drive shafts to be interchangeable. After the LCP fibers are wound over the mandrel 62, and the binding material has cured, the mandrel 62 is pulled on each end to reduce its diameter and to release the drive shaft. The angle at which the LCP fibers are braided or wound over the mandrel may be manipulated in a manner to vary the torque and flexibility aspects of the drive shaft. Similarly, the number of fiber layers 64 or the binding material that holds the fibers together can also be varied to change torques and flexibilities over the length of the drive shaft.

Utilizing an LCP material allows the drive shaft to be made fluid tight to segregate a guide wire lumen in the center of the drive shaft from the sheath lumen enclosing the drive shaft. As will be appreciated by those of ordinary skill in the art, many different LCPs or polymeric materials such as could be used to construct a drive shaft as long as the torque carrying capability and flexibility is sufficient to control the drive shaft.

Figure 5A:
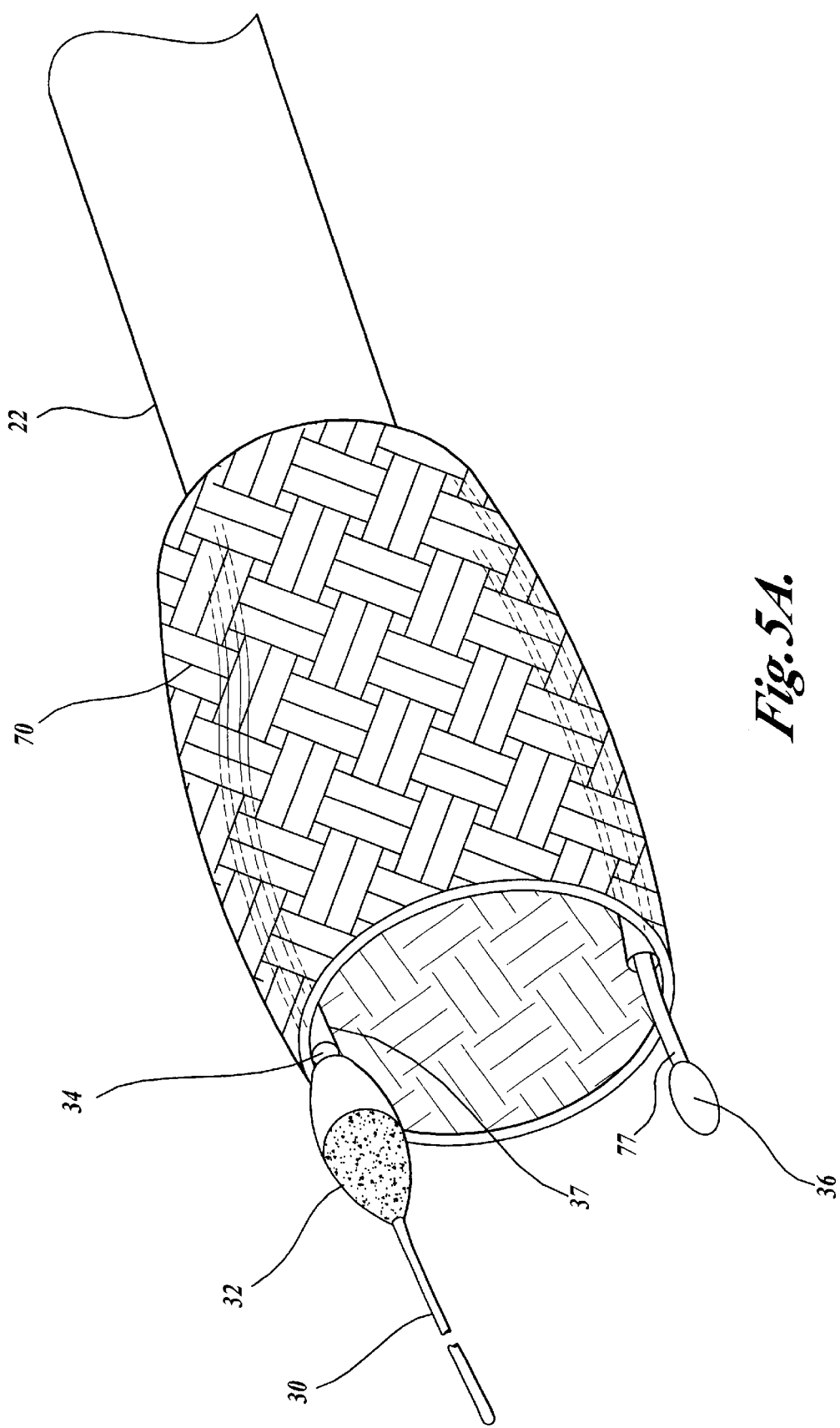
FIGS. 5A–5E illustrate a combination ablation/imaging atherectomy device and its operation according to the present invention.

As indicated above, another common problem with atherectomy devices is fitting the device with the correct sized burr to create the desired lumen in a patient's vessel. As shown in FIG. 5A, an ablation device according to the present invention has an expandable distal end allowing it to fit within virtually any vessel in order to create a maximum sized lumen without having to use more than one ablation burr. The catheter 22 has a self-expanding mesh or slent 70 disposed at its distal end. The mesh 70 is preferably made of the same material used to create self-expanding wall stents. One end of the self-expanding mesh is secured within the distal end of the catheter 22 while the distal end of the self-expanding mesh is allowed to fully expand.

The distal ends of the wires that comprise the mesh 70 are preferably atraumatic to avoid damaging a vessel wall. The tips are made atraumatic by forming balls on the ends of the wires that comprise the mesh or by joining the ends of the meshwire to a collapsible ring that has a smooth outer surface. The ablation burr 32 is mounted on a distal end of the drive shaft 34, which in turn is routed through a lumen 37 on the inner wall of the catheter 22.

Also included in the catheter 22 is the imaging device, such as an IVUS 36. The IVUS 36 may be guided in many different ways. For example, the IVUS 36 may be connected to a distal end of a guide wire (not shown) and routed through a second lumen 77 on the inner wall of the catheter 22.

The lumen 37 through which the ablation burr 32 is routed and the lumen 77 through which the imaging device is routed, are preferably spaced part and fixed to the self-expanding mesh so they maintain their relative position as the catheter 22 is moved. The self-expanding mesh 70 expands to fill the lumen of the vasculature in which the atherectomy device is placed.

Figure 5B:
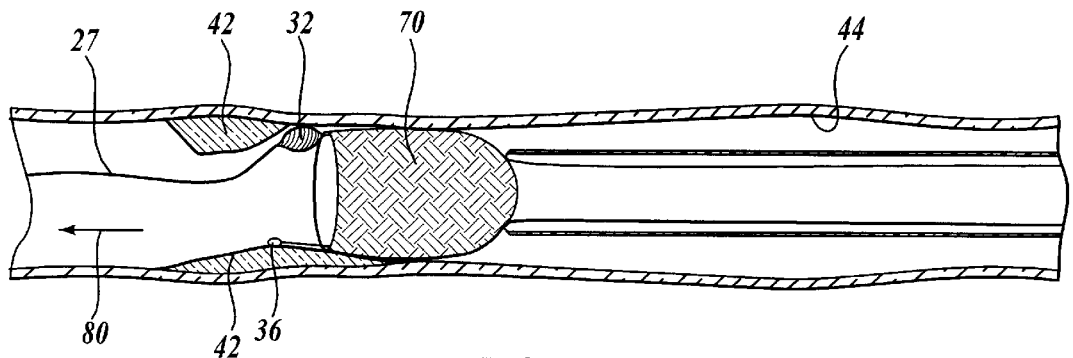

FIGS. 5B through 5E illustrate how the atherectomy device shown in FIG. 5A is guided through a stenosis. The catheter 22 including expandable mesh 70 is preferably drawn into a surrounding sheath (not shown) that collapses the mesh. Upon reaching the stenosis, the catheter 22 and self-expanding mesh 70 are pushed out of the sheath so that the mesh 70 expands. FIG. 5B illustrates an atherectomy device upon reaching a stenosis 42. The self-expanding mesh 70 has expanded to contact the inner walls 44 of the vasculature. As the burr 32 is rotated, a portion of the stenosis 42 is ablated. As will be appreciated, in order to ablate a full 360° lumen within the patient's vessel, the catheter 22 including the self expanding mesh 70 must be rotated either 360° or back and forth over 180°+. In that case, it may be desirable to coat the self-expanding mesh 70 with a lubricous coating such as PTFE (e.g., Teflon®), POC or other slippery material. If the entire catheter 22 and self-expanding mesh 70 rotates in the vessel, the lumens 37 and 77 that drive shaft 34 and IVUS 36 are fixed to the self-expanding mesh 70 either by spot welding them to the mesh or a marker band using surrounding the mesh. Alternatively, the lumens 37 and 77 may be held in the mesh by stitching them to the mesh with wire or other material.

As an alternative, the catheter 22 and self-expanding mesh 70 may remain fixed in the vessel and only the lumens that carry the ablation burr and the IVUS may be rotated. However, this approach is generally not preferred because the self-expanding mesh 70 must be withdrawn into the surrounding sheath in order to advance the catheter 26 within the vessel.

Figure 5C:
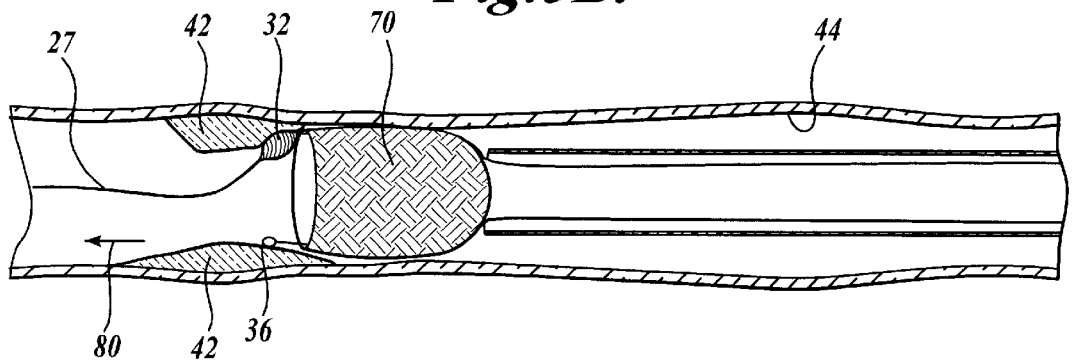

FIG. 5C illustrates the ablation burr 32 beginning to ablate the stenosis 42. The atherectomy device has moved distally, placing the ablation burr 32 in further contact with the stenosis 42. While the stenosis 42 is being ablated, the IVUS 36 produces images of the interior of the vessel wall that are used to help ensure that the stenosis 42 is being removed completely before the ablation burr is advanced further.

Figure 5D:
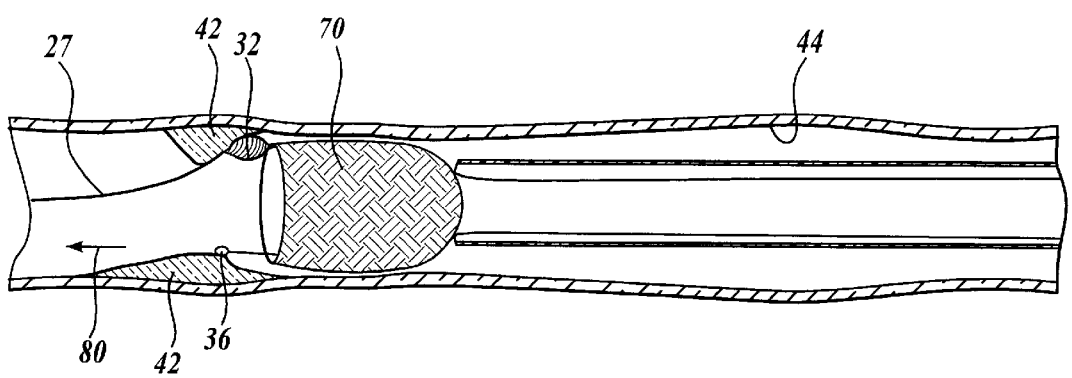
Figure 5E:
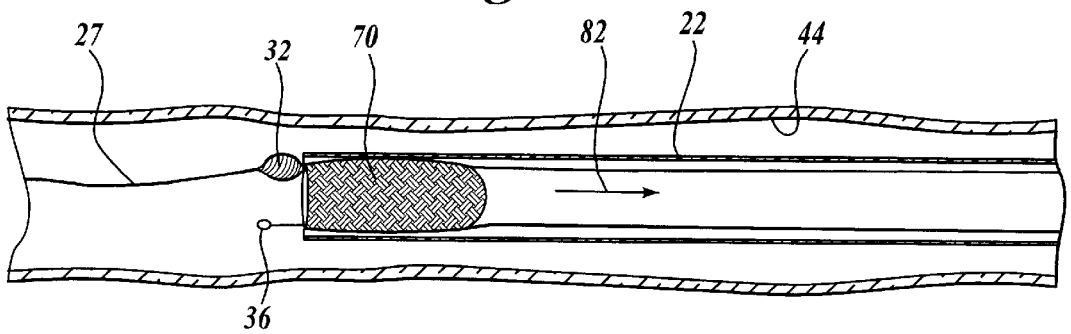

FIG. 5D illustrates the atherectomy device approximately through one-third of the stenosis 42 while FIG. 5E illustrates the stenosis 42 completely ablated. After removing the stenosis 42, the self-expanding mesh 70 is moved in the direction of the arrow 82 (toward the proximal end of the catheter 22) and into a sheath such that the mesh 70 is collapsed and may be withdrawn into the lumen of the catheter 22. The catheter is then withdrawn from the patient.

Figure 6:
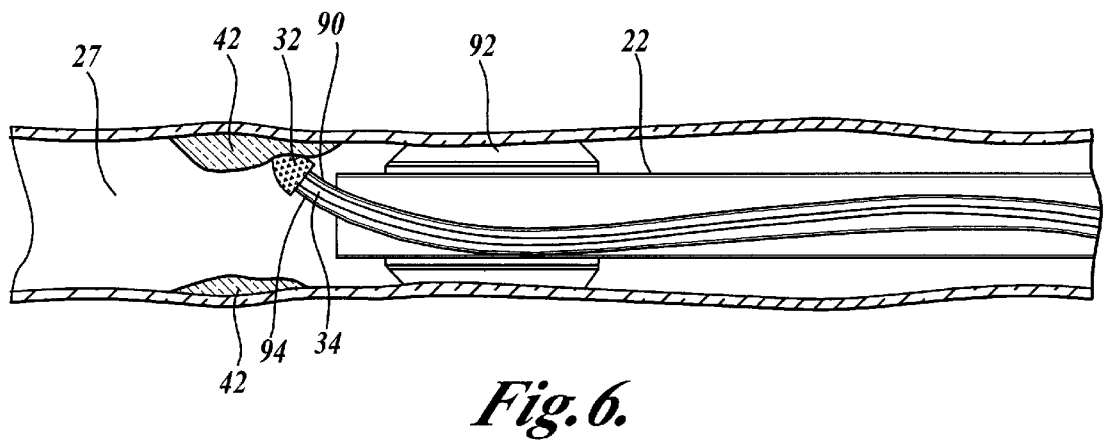
FIG. 6 is a view of an atherectomy device utilizing a control shaft having a predefined bend at its distal end to control the diameter of a lumen that is created with an ablation burr in accordance with another aspect of the present invention.

FIG. 6 illustrates another embodiment of an atherectomy device according to the present invention. In this embodiment, a torque resistant control shaft 94 has a pre-defined bend at its distal end and displaces the ablation burr 32 laterally in the vessel. A drive shaft 34 is contained within the lumen of the torque resistant control shaft 94 and rotates the ablation burr 32 as described above. An occluding balloon 92 at the distal end of the catheter 22 is inflated to maintain the position of a catheter 22 in the vessel while the stenosis 42 is ablated. As the predefined bend at the distal end of the torque resistant control shaft 94 is moved with respect to the distal end of the catheter 22, the amount of lateral displacement of the burr 32 either increases or decreases. The torque resistant control shaft 94 may include one or more radiopaque marker bands that can be viewed by a physician with fluoroscopy in order to detect how far the control shaft extends from the distal end of the catheter 22 and therefore what diameter lumen will be created.

Figure 7A:
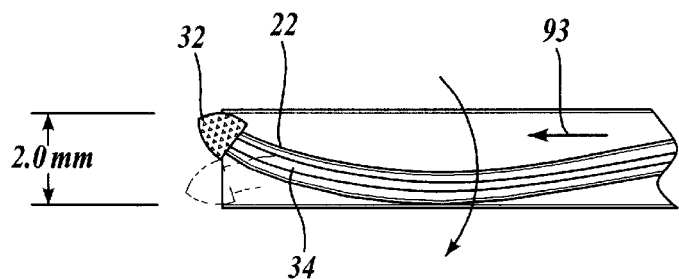
FIGS. 7A–7C illustrate the operation of the control shaft to create different sized lumens in a vessel.

FIG. 7A illustrates that the diameter of the ablation path may be limited to the diameter of the catheter 22 surrounding the control shaft 94 by withdrawing the bend of the control shaft into the lumen of the catheter 22. In one particular embodiment, the diameter of the ablation guide catheter 22 is 2.0 mm. As will be appreciated by those of ordinary skill in the art, the ablation guide catheter 22 can be made many different sizes.

Figure 7B:
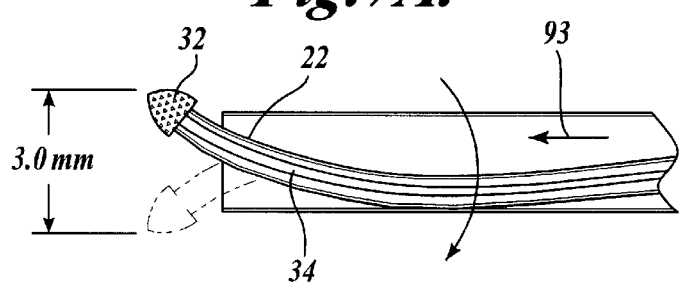

FIG. 7B illustrates that as the torque resistant, control shaft 94 is moved distally in the direction of the arrow 92, such that more of the predefined bend extends out the distal end of the catheter 22, the lateral displacement of the burr 32 increases. In this particular example, as the control shaft 94 is rotated in the catheter 22, the diameter of the lumen created by the ablation burr is 3.0 mm. To create a 360° lumen in the vessel, the torque resistant control shaft 94 is rotated within the catheter 22.

Figure 7C:
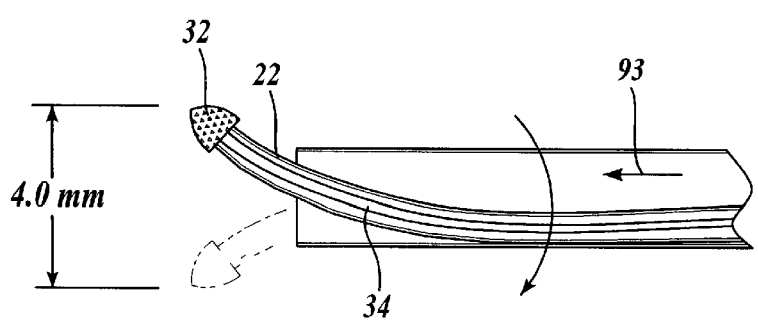

FIG. 7C illustrates that as the predefined bend in the torque resistant control shaft 94 is moved further distally to extend outside of the distal end of ablation guide catheter 22, the ablation burr extends further laterally in the vessel. As will be appreciated by those of ordinary skill in the art, almost any lumen diameter may be created during operation of the atherectomy device by extending or retracting the predefined bend into or out of the guide catheter. As long as the torque resistant control shaft 94 maintains its rigidity, any diameter lumen may be created.

While the preferred embodiment of the invention has been illustrated and described, it will be appreciated that various changes can be made therein without departing from the scope of the invention. It is therefore intended that the scope of the invention be determined from the following claims and equivalents thereto.

The embodiments of the invention in which an exclusive property or privilege is claimed are defined as follows:

1. An atherectomy device, comprising:
    a catheter including an expandable stent at the distal end of the catheter; and
    a drive shaft having an ablation burr at its distal end, the drive shaft being routed within the catheter and rotatably secured to one side of the expandable stent such that the expandable stent forces the ablation burr against a vessel wall whereby rotation of the stent in the vessel causes the ablation burr to create a lumen in the vessel having a diameter that is larger than a diameter of the burr.

2. The atherectomy device of claim 1, further comprising an imaging device disposed on a guide wire that is routed within the catheter for imaging an interior of the vessel wall.

3. The atherectomy device of claim 2, wherein the imaging device is an IVUS.

4. The atherectomy device of claim 2, wherein the drive shaft and imaging device are routed through separate lumens of the catheter, each of the lumens being secured to the expandable stent.

5. The atherectomy device of claim 1, wherein the drive shaft is made of braided or wound fibers of a liquid crystal polymer material.

6. The atherectomy device of claim 1, wherein the drive shaft h as a proximal end and a distal end, the distal end of the drive shaft being coated with an elastomer.

7. The atherectomy device of claim 1, wherein the drive shaft comprises:
   a proximal portion;
   a distal portion covered by an elastomer; a and
   a coupler that joins the distal portion to the proximal portion.

* * * * *

UNITED STATES PATENT AND TRADEMARK OFFICE
CERTIFICATE OF CORRECTION

PATENT NO.    : 6,497,711 B1
DATED         : December 24, 2002
INVENTOR(S)   : M. Plaia et al.

It is certified that error appears in the above-identified patent and that said Letters Patent is hereby corrected as shown below:

Title page Item [54] and Column 1, lines 1-3,
"THERECTOMY DEVICE HAVING A LIGHT WEIGHT DRIVE SHAFT AND AN IMAGING DEVICE" should read -- ATHERECTOMY DEVICE HAVING A LIGHT WEIGHT DRIVE SHAFT AND AN IMAGING DEVICE --

Title page,
Item [74], *Attorney, Agent, or Firm*, "Christensen, 0'Connor, Johnson, Kindness, PLLC" should read -- Christensen O'Connor Johnson Kindness PLLC --

Column 8,
Line 5, "h as" should read -- has --
Line 9, "elastomer; a and" should read -- elastomer; and --

Signed and Sealed this

Twenty-second Day of July, 2003

JAMES E. ROGAN
*Director of the United States Patent and Trademark Office*